(12) United States Patent
Cheim

(10) Patent No.: US 11,867,683 B2
(45) Date of Patent: Jan. 9, 2024

(54) SYSTEMS AND METHODS FOR DISSOLVED GAS ANALYSIS

(71) Applicant: Hitachi Energy Ltd, Zürich (CH)

(72) Inventor: Luiz Cheim, Raleigh, NC (US)

(73) Assignee: HITACHI ENERGY LTD, Zürich (CH)

( * ) Notice: Subject to any disclaimer, the term of this patent is extended or adjusted under 35 U.S.C. 154(b) by 355 days.

(21) Appl. No.: 16/804,923

(22) Filed: Feb. 28, 2020

(65) Prior Publication Data

US 2021/0270797 A1 Sep. 2, 2021

(51) Int. Cl.
*G01N 33/28* (2006.01)
*H01F 27/12* (2006.01)
*H01F 27/40* (2006.01)
*H02H 7/04* (2006.01)
*G01N 21/3504* (2014.01)

(52) U.S. Cl.
CPC ..... *G01N 33/2841* (2013.01); *G01N 21/3504* (2013.01); *H01F 27/12* (2013.01); *H01F 27/402* (2013.01); *H02H 7/04* (2013.01); *H01F 2027/404* (2013.01)

(58) Field of Classification Search
CPC ...... H01F 27/12; H02H 7/04; G01N 33/2841; G01N 21/3504
See application file for complete search history.

(56) References Cited

U.S. PATENT DOCUMENTS

| | | | |
|---|---|---|---|
| 2009/0187344 A1* | 7/2009 | Brancaccio | G01R 19/2513 702/58 |
| 2014/0260529 A1* | 9/2014 | Pruente | G01N 33/2888 73/19.11 |
| 2015/0081599 A1 | 3/2015 | Dobler | |
| 2018/0299375 A1* | 10/2018 | Young | G01N 15/0656 |

FOREIGN PATENT DOCUMENTS

| | | |
|---|---|---|
| CN | 103399237 A | 11/2013 |
| CN | 107884647 A | 4/2018 |

OTHER PUBLICATIONS

"Gradient Boosting vs Random Forest"—Abolfazl Ravanshad. URL: https://medium.com/@aravanshad/gradient-boosting-versus-random-forest-cfa3fa8f0d80 (Year: 2018).*

(Continued)

*Primary Examiner* — Benjamin R Schmitt
(74) *Attorney, Agent, or Firm* — Sage Patent Group

(57) ABSTRACT

A method of analyzing dissolved gas in an oil-filled transformer includes determining a centroid of a polygon that represents a plurality of dissolved gas concentrations. A fault region in which the centroid of the polygon is located is determined, where the plurality of fault regions are defined in a composite fault region map that is a composite of a Duval Pentagons 1 and 2. The method classifies a fault experienced by the transformer based on the determined fault region within the composite fault region map. The classification is done by a machine learning classification technique. Further embodiments classify faults based on (Continued)

dissolved gas levels without determining a centroid of a polygon representing the dissolved gas levels. Related systems are also disclosed.

17 Claims, 12 Drawing Sheets

(56) References Cited

OTHER PUBLICATIONS

"Decision Tree vs Random Forest vs Gradient Boosting Machines: Explained Simply"—Stephanie Glen. URL: https://medium.com/@aravanshad/gradient-boosting-versus-random-forest-cfa3fa8f0d80 (Year: 2019).*
"Stochastic Gradient Boosting"—Jerome Friedman. (Year: 1999).*
Duval, M. and Lamarre, L.,"The Duval Pentagon—A New Complementary Tool for the Interpretation of Dissolved Gad Analysis in Transformers," IEEE Electrical Insulation Magazine, vol. 30, No. 6, pp. 9-12, Nov.-Dec. 2014, 4 pages.
International Search Report and Written Opinion of the International Searching Authority, PCT/EP2021/054951, dated Jul. 21, 2021, 17 pages.
Cheim, Luiz et al., "Combined Duval Pentagons: A Simplified Approach", Energies, vol. 13, No. 11, Jun. 3, 2020, 12 pages.
Benmahamed, Y. et al., "Application of SVM and KNN to Duval Pentagon 1 for transformer Oil Diagnosis", IEEE Transactions on Dielectrics and Electrical Insulation, vol. 24, No. 6, Dec. 2017, 9 pages.
Canadian Office Action for Canadian Application No. CA 3148790 dated Jun. 1, 2023, 4 pages.
First Chinese Office Action for Chinese Application No. CN 202180006923.6 dated Jul. 8, 2023, 15 pages (including English translation, Chinese Search Report and Report Letter).
Wang, Jianyi et al., "Study on Fault Severity Evaluation Method for Power Transformer Based on Energy Intensity", China Academic Journal Electronic Publishing House, 2018, 7 pages (including English translation).

* cited by examiner (a)

(b)

SYSTEMS AND METHODS FOR DISSOLVED GAS ANALYSIS

BACKGROUND

The present disclosure relates to fault analysis for oil-filled transformers. In particular, the present disclosure relates to systems and methods for performing dissolved gas analysis (DGA) for classifying faults in oil-filled transformers.

Some electrical equipment, such as high voltage transformers, include oil-filled chambers, where the oil in the transformer serves a number of functions. The oil may act as a coolant and/or an insulator, and may protect cellulose (paper) in the transformer from chemical attack. The oil may also help prevent sludge buildup within the transformer. Finally, the oil may be used as a diagnostic tool for identifying and classifying faults that may occur in the transformer.

Typically, mineral oil, such as naphthenic oil or paraffinic oil, is used in transformer, with naphthenic oil generally being preferred because, although its oxidation rate is larger than paraffinic oil, the oxidation products of naphthenic oil are soluble and therefore less likely to form precipitates that could interfere with cooling. Synthetic oil may also be used in some transformers.

Oil-filled transformers may experience faults during operation due to various causes, such as over-voltage conditions, over-temperature conditions, electrical discharges, or other reasons. When a fault occurs, it is desirable to identify the nature and/or severity of the fault to determine whether corrective action is indicated, and if so, what type of corrective action is needed.

Faults in oil-filled transformers can be classified in various ways. Typically, faults are classified based on the nature of the conditions experienced by the transformer when the fault occurred. For example, a fault may be classified according to the temperature associated with the fault, whether electrical discharge occurred in connection with the fault, whether a corona partial discharge occurred in connection with the fault, whether carbonization of cellulose (paper) within the electrical device occurred, etc. Some types of faults are considered more serious than others, and may require more immediate or serious corrective action, up to and including shutting down or replacing the transformer.

When a fault occurs in an electrical device that contains a chamber filled with mineral oil, it is possible to characterize the type of fault by examining the relative portions of various dissolved gases within the oil. Such gases, which are sometimes referred to as diagnostic gases, may include, for example hydrocarbons such as Hz, $C_2H_2$, $C_2H_4$, $CH_4$, and $C_2H_6$. The relative concentrations of these gases in the oil can be used to determine what type of fault occurred, so that appropriate corrective action can be taken if needed.

SUMMARY

A method of analyzing dissolved gas in an oil-filled transformer includes obtaining measurements of dissolved gas levels of a first number of gases in the oil-filled transformer, determining relative levels of the first number of gases, and plotting a first number of points representing each of the relative levels of the first number of gases on a respective one of a first number of radial axes, each of the first number of radial axes being equally angularly spaced around an origin in a two dimensional coordinate system, each of the first number of radial axes representing a relative level of one of the first number of gases, the first number of points forming a polygon within the two dimensional coordinate system. The method further includes determining a centroid of the polygon. A fault region in which the centroid of the polygon is located is determined out of a plurality of fault regions defined in the two dimensional coordinate system, wherein the plurality of fault regions are defined in a composite fault region map that is a composite of a first fault region map that defines regions that classify basic electrical faults within the oil-filled transformer, wherein the definition of regions in the first fault region map is not based on carbonization of cellulose within the oil-filled transformer, and a second fault region map that defines regions that classify faults at least partially based on carbonization of cellulose within the oil-filled transformer. The method further includes classifying a fault experienced by the oil-filled transformer based on the determined fault region within the composite fault region map.

In some embodiments, the first number is five, the polygon includes a pentagonal shape, the first fault region map includes a first Duval pentagon, and the second fault region map includes a second Duval pentagon.

In some embodiments, the composite fault region map includes regions that classify thermal faults based on both thermal properties and carbonization of cellulose within the oil-filled transformer.

In some embodiments, the first Duval pentagon defines fault regions based on temperature, the second Duval pentagon defines fault regions based at least in part on carbonization, and the composite fault region map defines fault regions based on a combination of temperature and carbonization.

In some embodiments, the first Duval pentagon defines fault regions of T1, T2, and T3, the second Duval pentagon defines fault regions of O, C, and T3-H, and the composite fault region map defines fault regions that are coterminous within the fault regions of T1, T2 and T3 in the first Duval pentagon and the fault regions of O, C, and T3-H in the second Duval pentagon.

In some embodiments, the fault regions within the composite fault region map include T1-O, T2-O, T1-C, T2-C, T3-C and T3-H.

In some embodiments, the first number of gases include $C_2H_2$ plotted on a first axis that extends at an angle of 18 degrees relative to an x-axis of the two dimensional coordinate system, $H_2$ plotted on a second axis that extends at an angle of 90 degrees relative to the x-axis of the two dimensional coordinate system, $C_2H_6$ plotted on a third axis that extends at an angle of 162 degrees relative to the x-axis of the two dimensional coordinate system, $CH_4$ plotted on a fourth axis that extends at an angle of 234 degrees relative to the x-axis of the two dimensional coordinate system, and $C_2H_4$ plotted on a fifth axis that extends at an angle of 306 degrees relative to the x-axis of the two dimensional coordinate system.

In some embodiments, the fault regions within the composite fault region map have the following coordinates in the two-dimensional coordinate system wherein the relative levels of the first number of gases are plotted as relative percentages of the first number of gases:

T1-O: [(−35, 3.1), (0, 1.5), (0, −3), (−3.5, −3.5), (−6, −4), (−11, −8), (−18.8, −26), (−22.5, −32.4), (−23.5, −32.4)]

T2-O: [(−21.5, −32.4), (−18.8, −26), (−22.5, −32.4)]

T1-C: [(−6, −4), (−11, −8), (−18.8, −26)]

T2-C: [(−6, −4), (−18.8, −26), (−21.5, −32.4), (1, −32.4)]

T3-C: [(−3.5, −3.5), (−6, −4), (1, −32.4), (2.5, −32.4)]

T3-H: [(−3.5, −3.5), (2.5, −32.4), (23.5, −32.4), (24.3, −30), (0, −3)].

In some embodiments, determining the fault region in which the centroid of the polygon is located includes inputting the centroid of the polygon into a machine learning classification technique that generates, as an output, a classification of the fault region associated with the centroid.

In some embodiments, the machine learning classification technique was trained via supervised learning using an input data set including a plurality of centroids and associated fault regions.

In some embodiments, the machine learning classification technique includes a random forest technique. In some embodiments, the machine learning classification technique includes a gradient boosting machine technique.

The method may further include activating an alarm in response to classifying the fault. The method may include deactivating the oil-filled transformer in response to classifying the fault.

In some embodiments, obtaining measurements of dissolved gas levels of the first number of gases in the oil-filled transformer includes receiving sensor measurements from a sensor in the oil-filled transformer.

A method of training a machine classification learning technique includes generating a plurality of sets of artificial dissolved gas concentrations of a first number of diagnostic gases, determining relative levels of the artificial dissolved gas levels, plotting a first number of points representing each of the relative levels of the first number of gases on a respective one of a first number of radial axes, each of the first number of radial axes being equally angularly spaced around an origin in a two dimensional coordinate system, each of the first number of radial axes representing a relative level of one of the first number of gases, the first number of points forming a polygon within the two dimensional coordinate system, and determining a centroid of the polygon.

The method further includes determining a fault region in which the centroid of the polygon is located, out of a plurality of fault regions defined in the two dimensional coordinate system, classifying a fault experienced by the oil-filled transformer based on the determined fault region within the composite fault region map, and training a machine learning classification technique using the plurality of sets of artificial dissolved gas concentrations of a first number of diagnostic gases and associated faults as labeled training data.

In some embodiments, the plurality of fault regions are defined in a composite fault region map that is a composite of a first fault region map that defines regions that classify basic electrical faults within the oil-filled transformer that do not involve carbonization of cellulose within the oil-filled transformer and a second fault region map that defines regions that classify faults at least partially based on carbonization of cellulose within the oil-filled transformer.

In some embodiments, the machine learning classification technique includes a random forest technique and/or a gradient boosting machine technique.

In some embodiments, the method further includes obtaining measurements of dissolved gas levels in an oil-filled transformer, and classifying a fault of the oil-filled transformer using the machine learning classification technique.

In some embodiments, the method further includes activating an alarm in response to classifying the fault and/or deactivating the oil-filled transformer in response to classifying the fault.

In some embodiments, obtaining measurements of dissolved gas levels of the first number of gases in the oil-filled transformer includes receiving sensor measurements from a sensor in the oil-filled transformer.

A device according to some embodiments includes a processing circuit, and a memory coupled to the processing circuit. The memory includes computer readable program instructions that, when executed by the processing circuit, cause the device to obtain measurements of dissolved gas levels of a first number of gases in the oil-filled transformer, determine relative levels of the first number of gases, and plot a first number of points representing each of the relative levels of the first number of gases on a respective one of a first number of radial axes, each of the first number of radial axes being equally angularly spaced around an origin in a two dimensional coordinate system, each of the first number of radial axes representing a relative level of one of the first number of gases, the first number of points forming a polygon within the two dimensional coordinate system.

The device determines a centroid of the polygon, and determines a fault region in which the centroid of the polygon is located, out of a plurality of fault regions defined in the two dimensional coordinate system. The plurality of fault regions are defined in a composite fault region map that is a composite of a first fault region map that defines regions that classify basic electrical faults within the oil-filled transformer that do not involve carbonization of cellulose within the oil-filled transformer and a second fault region map that defines regions that classify faults at least partially based on carbonization of cellulose within the oil-filled transformer. The device classifies a fault experienced by the oil-filled transformer based on the determined fault region within the composite fault region map.

In some embodiments, the device is provided in a cloud-based service infrastructure, a standalone server or a server cluster. In some embodiments, the device is connectable to a sensor and/or a dissolved gas analyzer for obtaining the measurements of dissolved gas levels in the oil-filled transformer.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings.

DETAILED DESCRIPTION

Inventive concepts will now be described more fully hereinafter with reference to the accompanying drawings, in which examples of embodiments of inventive concepts are shown. Inventive concepts may, however, be embodied in many different forms and should not be construed as limited to the embodiments set forth herein. Rather, these embodiments are provided so that this disclosure will be thorough and complete, and will fully convey the scope of present inventive concepts to those skilled in the art. It should also be noted that these embodiments are not mutually exclusive. Components from one embodiment may be tacitly assumed to be present/used in another embodiment.

The following description presents various embodiments of the disclosed subject matter. These embodiments are presented as teaching examples and are not to be construed as limiting the scope of the disclosed subject matter. For example, certain details of the described embodiments may be modified, omitted, or expanded upon without departing from the scope of the described subject matter.

Figure 1:
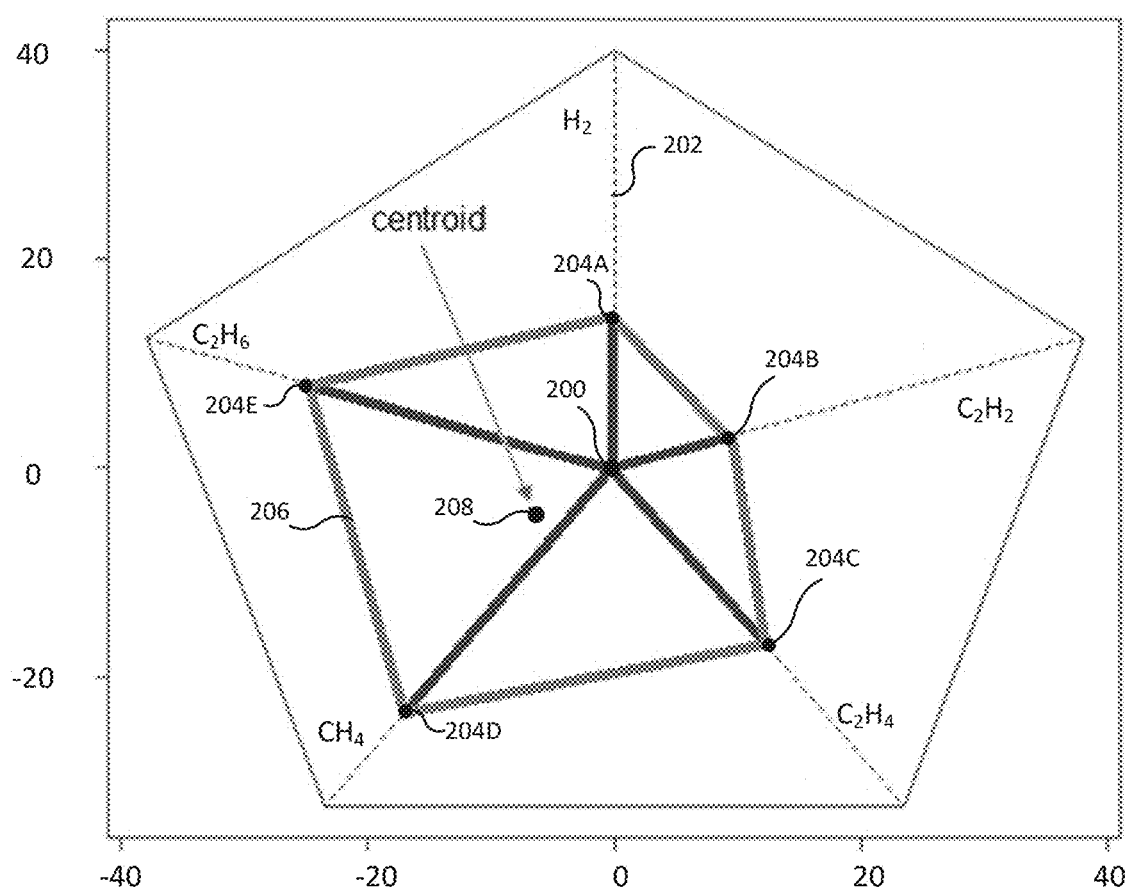
FIG. 1 is a graph on which relative concentrations of five diagnostic gases are plotted to form a polygon for purposes of dissolved gas analysis.

As noted above, the presence of dissolved gases within oil-filled transformers can be used as a diagnostic tool to classify faults experienced by the transformer. An approach that has gained wide acceptance in the art is known as the Duval Pentagon classification. Referring to FIG. 1, in the Duval Pentagon classification approach, the relative concentrations of five diagnostic gases, namely, Hz, $C_2H_2$, $C_2H_4$, $CH_4$, and $C_2H_6$ are plotted in a cartesian plane defined by an x-axis and a y-axis, where each relative concentration is plotted along one of five radial axes 202 that are equally spaced about an origin 200. That is, each of the five radial axes 202 corresponds to one of the diagnostic gases, and five points 204A-204E are plotted along the five radial axes 202, the five points 204A-204E representing the relative concentrations of the respective gases as percentage values.

The five radial axes 202 are spaced at equal angles around the origin 200 in the two-dimensional cartesian coordinate system. In particular, the five axes 202 may include a first axis that extends at an angle of 18 degrees relative to the x-axis on which $C_2H_2$ is plotted, a second axis that extends at an angle of 90 degrees relative to the x-axis on which $H_2$ is plotted, a third axis that extends at an angle of 162 degrees relative to the x-axis on which $C_2H_6$ is plotted, a fourth axis that extends at an angle of 234 degrees relative to the x-axis on which $CH_4$ is plotted, and a fifth axis that extends at an angle of 306 degrees relative to the x-axis on which $C_2H_4$ is plotted.

The relative concentration of a gas may be calculated by dividing the concentration of the gas (in parts per million, ppm) by the total concentration of all five gases in ppm. For example, the relative percentage of $H_2$ may be calculated as shown in Eq. 1:

$$100 \times (\text{ppm of } H_2)/(\text{ppm of } H_2+CH_4+C_2H_6+C_2H_4+C_2H_2) \quad [1]$$

The resulting five points 204A to 204E form a polygon 206 in the cartesian plane defined by the x-axis and the y-axis. According to the Duval Pentagon classification approach, a centroid 208 is calculated for the polygon 206. The location of the centroid 208 may be calculated according to Equation [2] as follows:

$$C_x = \frac{1}{6A}\sum_{i=0}^{n-1}(x_i + x_{i+1})(x_i y_{i+1} - x_{i+1} y_i) \quad [2]$$

$$C_y = \frac{1}{6A}\sum(y_i + y_{i+1})(x_i y_{i+1} - x_{i+1} y_i),$$

where $C_x$ is the x-coordinate of the centroid 208 and $C_y$ is the y-coordinate of the centroid 208, and $(x_i, y_i)$ are the coordinates of the five points 204A-204E, and A is the area of the polygon 206, given by Equation [3] as:

$$A = \frac{1}{2}\sum_{i=0}^{n-1}(x_i y_{i+1} - x_{i+1} y_i). \quad [3]$$

The coordinates of the centroid 208 can be calculated in other ways, such as by calculating the averages of the x- and y-coordinates of the points 204A-204E.

Figure 2:
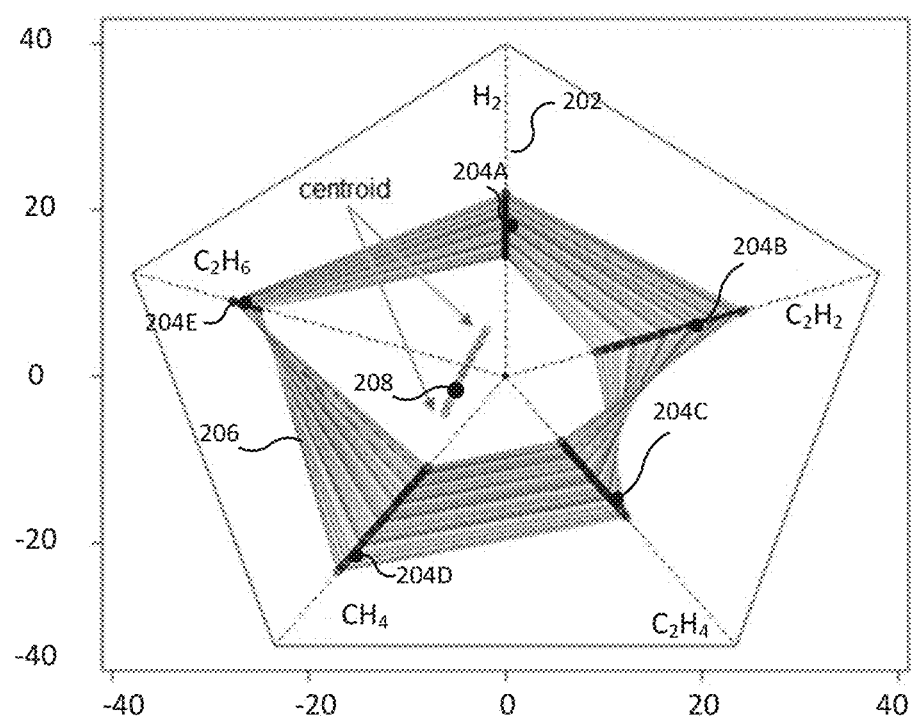
FIG. 2 is a graph illustrating how a location of a centroid of the polygon changes as relative concentrations of five diagnostic gases are varied.

Accordingly, the location of the centroid 208 depends on the locations of the points 204A-204E, which in turn depends on the relative concentrations of each of the five diagnostic gases. As can be seen in FIG. 2, as the relative concentrations of each of the five diagnostic gases are varied, there is a corresponding change in the location of the centroid 208. It will be further appreciated that the centroid 208 of a polygon 206 is not unique; that is, two different polygons 206 may have the same centroid.

The order of gases on the five radial axes 202 corresponds to the increasing energy required to produce these gases in transformers, from $H_2$ to $C_2H_2$, counterclockwise in FIG. 1. The coordinates of the 100% levels for Hz, $C_2H_6$, $CH_4$, $C_2H_4$, and $C_2H_2$ shown in FIG. 1 are (0, 100), (−95.1, 30.9), (−58.8, −80.9), (58.8, −80.9), and (95.1, 30.9), respectively. However, it will be appreciated that even when the relative percentage is 100% for one gas, e.g., Hz, and 0% for the other gases, the centroid will be at no more than 40% on the $H_2$ axis. Thus, the polygon 206 will fall within a region that is bounded by the five axes extending to no greater than 40% concentration levels.

Figure 3A:
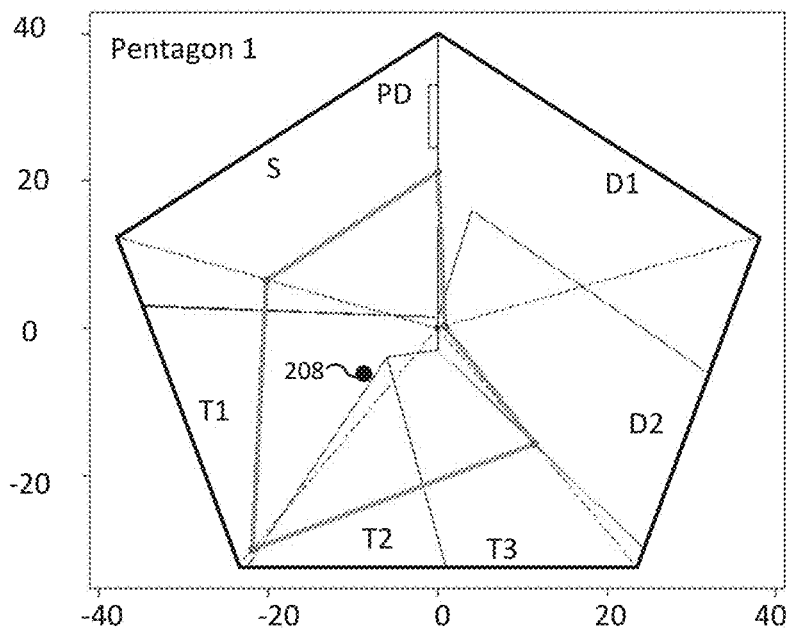
FIG. 3A illustrates plotting the centroid on Duval Pentagon 1.
Figure 3B:
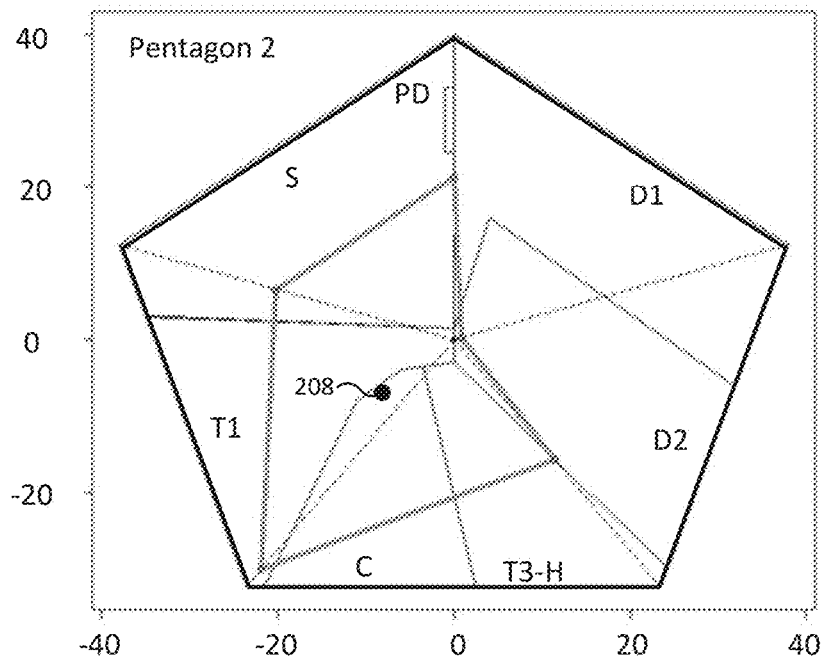
FIG. 3B illustrates plotting the centroid on Duval Pentagon 2.

The location of the centroid 208 of the polygon 206 is used as a diagnostic tool by plotting the centroid 208 on a fault region map, such as one of two Duval Pentagons. The two Duval Pentagon fault region maps, Duval Pentagon 1 and Duval Pentagon 2, are shown in FIGS. 3A and 3B, respectively. Each Duval Pentagon is divided into seven fault regions. In general, Duval Pentagon 1 defines fault regions that classify basic electrical faults within the oil-filled transformer that do not indicate whether carbonization of cellulose within the oil-filled transformer occurred, while Duval Pentagon 2 defines fault regions that classify faults at least partially based on carbonization of cellulose within the oil-filled transformer.

In Duval Pentagon 1, the fault regions are labeled S, PD, D1, D2, T1, T2 and T3. In Duval Pentagon 2, the fault regions are labeled S, PD, D1, D2, T3-H, C and O. The fault region labels in Duval Pentagon 1 have the following meanings:

S: Stray gassing of mineral oil
PD: corona partial discharges
D1: low energy discharges
D2: high energy discharges
T1: thermal faults<300° C.
T2: thermal faults of between 300° C. and 700° C.
T3: thermal faults>700° C.
The fault regions labels in Duval Pentagon 2 have the following meanings:
S: Stray gassing of mineral oil
PD: corona partial discharges
D1: low energy discharges
D2: high energy discharges
O: Overheating<250° C.
C: thermal faults with carbonization of paper
T3-H: thermal faults in oil only (no carbonization of paper)

When a centroid falls within one of the fault regions of a Duval Pentagon, it is an indication of the type of fault that may have occurred in the transformer. Thus, for example, referring to FIG. 3A, the location of the centroid 208 falls within the T1 fault region of Duval Pentagon 1, indicating a thermal fault of less than 300° C. To fully classify the fault requires analysis of Duval Pentagon 2. Referring to FIG. 3B, the location of the centroid 208 falls within fault region C, indicating likely carbonization of cellulose (paper) material that is used as an insulator within the transformer. Although the fault is a relatively low temperature thermal fault, because carbonization indicates a potentially serious fault, some corrective action may be needed.

Because the Duval Pentagon analysis requires plotting the centroid on two different Duval Pentagons, the geometric analysis needed to classify a particular fault may be time consuming. In particular, the process described above requires many geometrical calculations to define the centroid of the irregular shape and a large number of <if-then-else> rules using coordinates of vertices of each diagnostic region and borderlines defined by the straight lines that form the limits between regions. These lines are different in Duval Pentagons 1 and 2. This process must be repeated whenever a new sample is available (such as a new manual DGA sample or a new data point from an online sensor). For fleet-wide condition assessment of transformers, this process may require thousands of calculations per hour in the case of online sensors and multiple transformers with those sensors.

Some embodiments described herein combine the two Duval Pentagons into a single composite fault region map with 9 (or 10) regions. Using a composite fault region map may eliminate the need to find two centers of gravity and perform two classifications for each sample. Some embodiments further generate a large number of centroids inside the composite fault region map and train a machine learning (ML) technique to classify centroids within the newly defined fault regions in the composite fault region map.

Some further embodiments described herein train a ML technique using supervised learning based on sampled or constructed dissolved gas data to classify transformer faults without reference to a fault region map. A fault region map, such as a composite fault region map, may be used to generate data points for supervised learning in the absence of sufficient available data.

Figure 4:
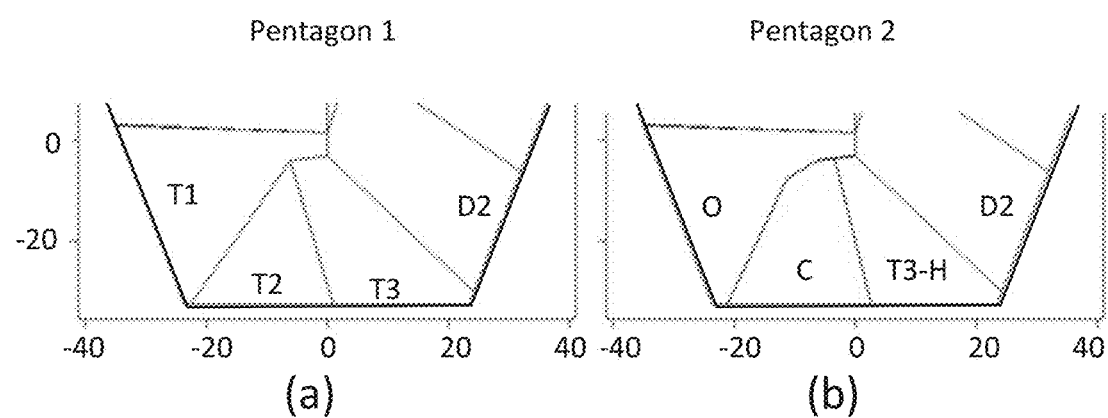
FIG. 4 is a detail illustration of portions of Duval Pentagon 1 and Duval Pentagon 2.

A composite fault region map may be constructed by overlaying the two Duval pentagons and defining regions within a single pentagon based on the regions defined in the two Duval pentagons. For example, FIG. 4 is a detail illustration the portions of the two Duval pentagons that differ from one another. As shown in FIG. 4, Duval Pentagon 1 defines regions T1, T2 and T3, while Duval Pentagon 2 defines regions O, C and T3-H in the same area as regions T1, T2 and T3 in Duval Pentagon 1.

Referring again to FIGS. 3A and 3B, the fault regions defined in Pentagon 1 are: PD, S, T1, T2, T3, D1 and D2, and the fault regions defined in Pentagon 2 are: PD, S, O, C, T3-H, D1 and D2. Importantly, dissolved gas analysis (DGA) points occurring in zone C of Pentagon 2 indicate a possibility of carbonization of paper, and thus further investigations with carbon oxides and furans should be undertaken. In about 10% of cases, carbonization of oil may occur rather than of paper.

It can be seen that regions PD, S, D1 and D2 are common and unchanged in both Pentagons. If only Pentagon 1 is analyzed, it can be determined that a low temperature thermal fault has occurred because the centroid is located in region T1. Looking to Pentagon 2, it is evident that a thermal issue with likely paper carbonization has occurred, since the centroid is located in region C.

As can be seen in FIGS. 3A and 3B, Pentagons 1 and 2 share the same geometry for regions PD, S, D1 and D2. The only significant difference between the two Pentagons occurs in the southern hemisphere involving thermal faults of type T1, T2 and T3 (Pentagon 1) that may be classified as O, C or T3-H in Pentagon 2.

FIG. 4 provides a more detailed view of the differences between the pentagons. A visual inspection of FIG. 4 indicates the significant changes in the thermal regions between Pentagons 1 and 2. The scales shown also illustrate the changes in the coordinates of individual vertices that form the fault regions. It can be seen, for example, that region T3-H in Pentagon 2 (high temperature fault in oil only) is somewhat narrower than T3 in Pentagon 1, meaning that not all faults classified as T3 occur in oil only. Some faults classified as T3 may involve paper carbonization C. Also, almost the entire fault region T2 is encompassed by C, meaning that most T2 faults involve paper carbonization. Finally, most, but not all T1 faults are of O type.

Figure 5:
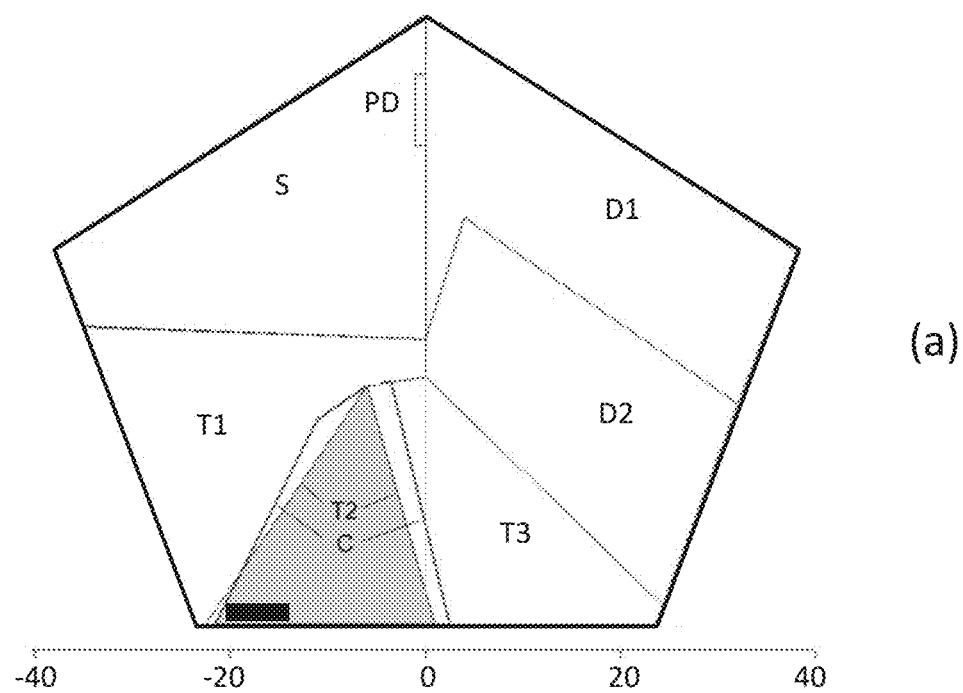
FIG. 5 illustrates how Duval Pentagon 1 and Duval Pentagon 2 can be combined to form a composite fault region map according to some embodiments.
Figure 5:
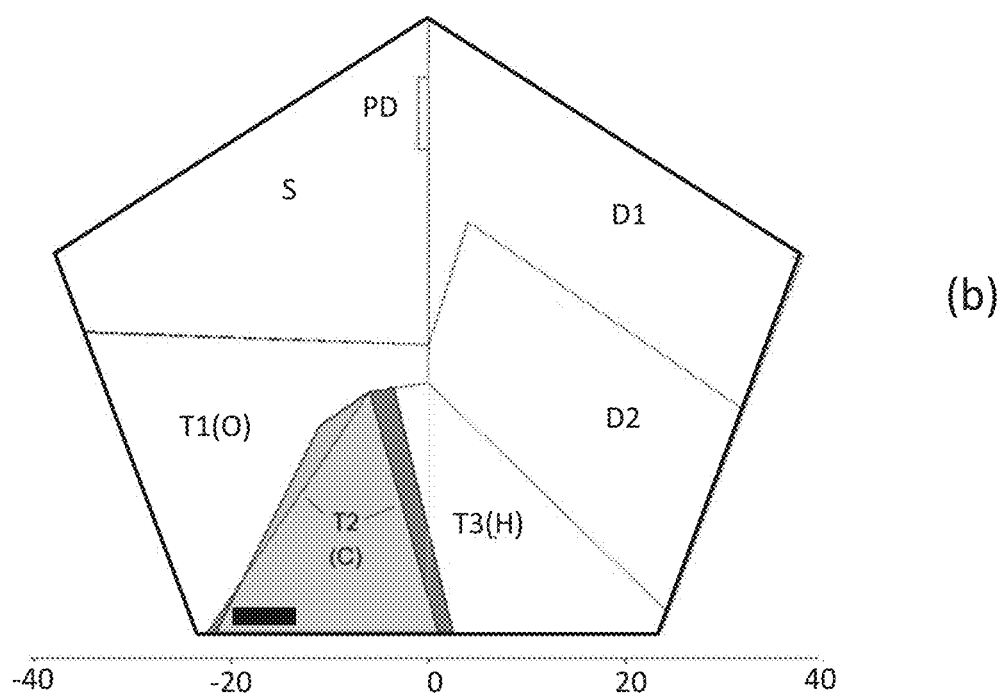

FIG. 5 illustrates the formation of a composite fault region map as a combination of Duval Pentagons 1 and 2. As can be seen from FIG. 5(b), there are 4 intersecting regions between region C in Pentagon 2 and T1, T2 and T3 in Pentagon 1. Three of those regions indicate paper carbonization associated to either T1, T2 or T3. One small region on the bottom left indicates thermal issues of T2 type that would fall outside the C zone in Pentagon 2. It is then possible to utilize the two combined Pentagons as above and define new names for the intersecting regions.

Figure 6:
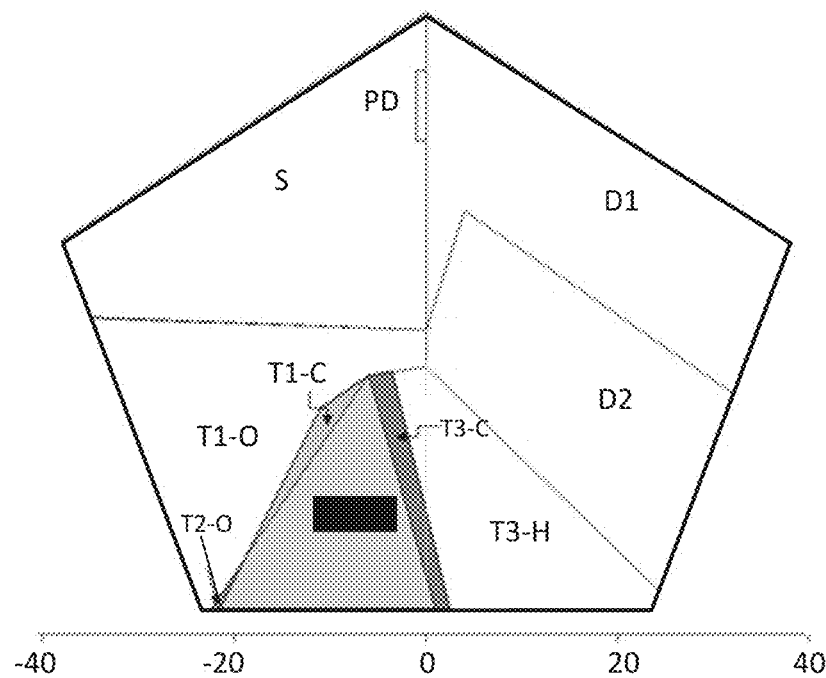
FIG. 6 illustrates a composite fault region map according to some embodiments.

Accordingly, as shown in FIG. 6, a composite fault region map can be constructed that defines the following new regions (listed with corresponding regions of the Duval pentagons):

T1-O: T1 in Pentagon 1, O in Pentagon 2
T1-C: T1 in Pentagon 1, C in Pentagon 2
T2-C: T2 in Pentagon 1, C in Pentagon 2
T2-O: T2 in Pentagon 1, O in Pentagon 2
T3-H: T3 in Pentagon 1, T3-H in Pentagon 2
T3-C: T3 in Pentagon 1, C in Pentagon 2

Figure 7:
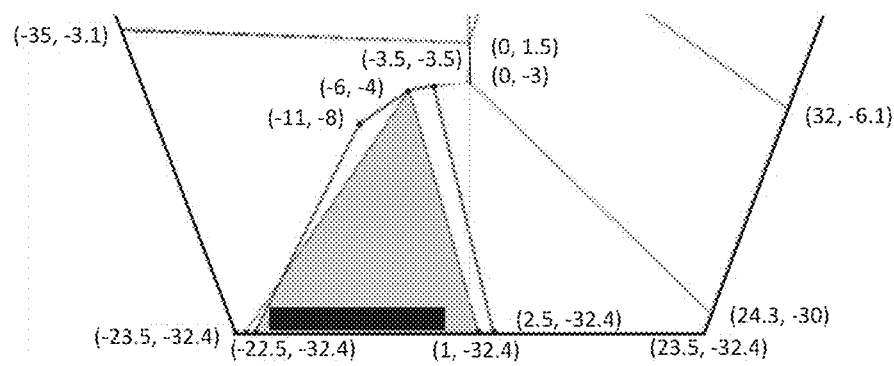
FIG. 7 illustrates regions of a composite fault region map according to some embodiments in more detail.

The coordinates of the new fault regions in the composite fault region map shown in FIG. 6 are illustrated in FIG. 7. The coordinates of the regions are as follows:

T1-O: [(−35, 3.1), (0, 1.5), (0, −3), (−3.5, −3.5), (−6, −4), (−11, −8), (−18.8, −26), (−22.5, −32.4), (−23.5, −32.4)]
T1-C: [(−6, −4), (−11, −8), (−18.8, −26)]
T2-C: [(−6, −4), (−18.8, −26), (−21.5, −32.4), (1, −32.4)]
T2-O: [(−21.5, −32.4), (−18.8, −26), (−22.5, −32.4)]
T3-H: [(−3.5, −3.5), (2.5, −32.4), (23.5, −32.4), (24.3, −30), (0, −3)]
T3-C: [(−3.5, −3.5), (−6, −4), (1, −32.4), (2.5, −32.4)]

Figure 8:
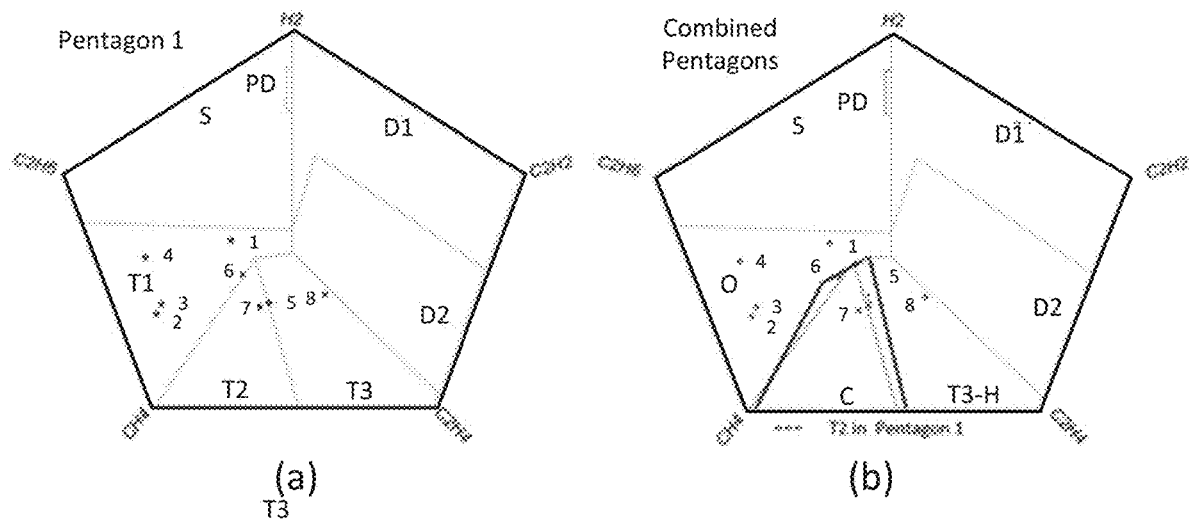
FIG. 8 illustrates the plotting of centroids on a composite fault region map according to some embodiments.

FIG. 8 illustrates the use of the composite fault region map to classify a plurality of data points represented by centroids 1 to 8. The classification is shown in Table 1, below.

TABLE 1

Classification using Composite Fault Region Map

| ID | H2 | CH4 | C2H2 | C2H4 | C2H6 | Pentagon 1 | Pentagon 2 | Composite |
|----|-----|------|------|------|------|------------|------------|-----------|
| 1  | 40  | 45   | 1    | 25   | 45   | T1         | O          | T1-O      |
| 2  | 0   | 150  | 0    | 5    | 70   | T1         | O          | T1-O      |
| 3  | 10  | 160  | 0    | 3    | 80   | T1         | O          | T1-O      |
| 4  | 10  | 200  | 0    | 20   | 310  | T1         | O          | T1-O      |
| 5  | 40  | 115  | 0    | 140  | 70   | T3         | C          | T3-C      |
| 6  | 360 | 610  | 9    | 260  | 259  | T1         | C          | T1-C      |
| 7  | 325 | 1200 | 0    | 1100 | 600  | T2         | C          | T2-C      |
| 8  | 30  | 17   | 0    | 250  | 60   | T3         | T3-H       | T3-H      |

FIG. 8(a) illustrates classification using Duval Pentagon 1 while FIG. 8(b) illustrates classification using Duval Pentagon 2 and the composite fault region map. As can be seen in FIG. 8, point 5 is classified as T3 in Pentagon 1, as C in Pentagon 2 and as T3-C in the composite fault region map. Point 6 classified as T1 in Pentagon 1, as C in Pentagon 2, and as T1-C in the composite fault region map.

To avoid complex and time consuming geometrical calculations, some embodiments train a machine learning classification technique to classify centroids according to the composite fault region map. The machine learning technique may be, for example, a classification technique. Many different classification techniques are known and can be used for the classification task, such as classification and regression tree techniques. In particular, a random forest technique or a gradient boost machine learning technique may be especially suited for this type of task.

The implementation of machine learning classification techniques is well known in the art. Typically, a classification technique is trained using supervised learning, in which a large number of labeled samples are input to the training technique. A problem arises in the implementation of a supervised training system for a classification technique in the context of DGA data, however, in that the number of available samples that can be used for training is limited. Accordingly, some embodiments generate random centroids to use as training data points and use the composite fault region map described above to generate training labels for the training data points. The classification technique is then trained using the resulting labeled training data.

Figure 9:
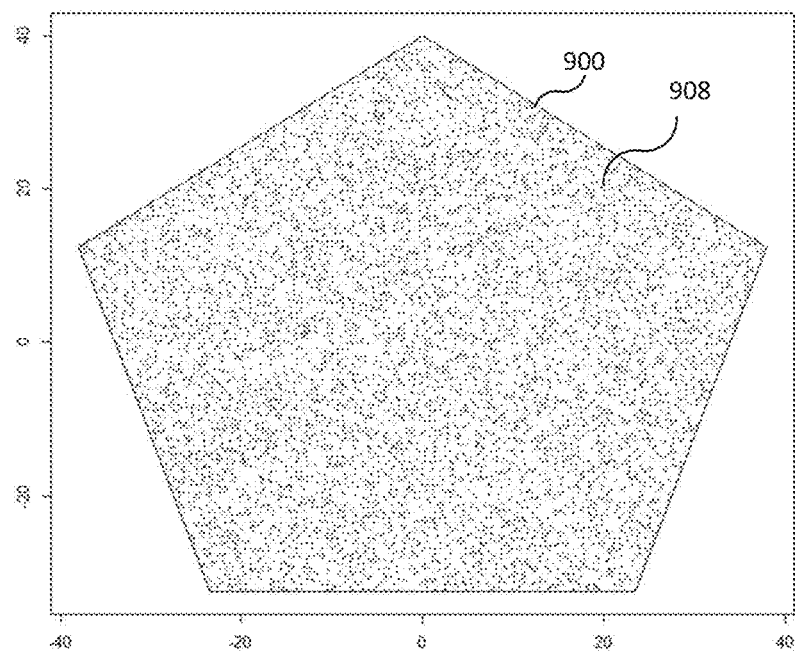
FIG. 9 illustrates generation of sample centroids for training a machine learning classification technique according to some embodiments.
Figure 10A:
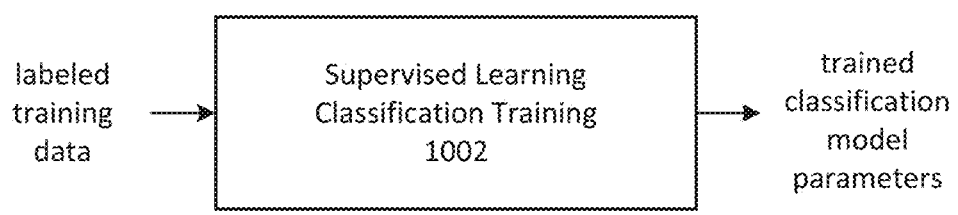
FIG. 10A illustrates a process of training a machine learning classification technique according to some embodiments using supervised learning.
Figure 10B:
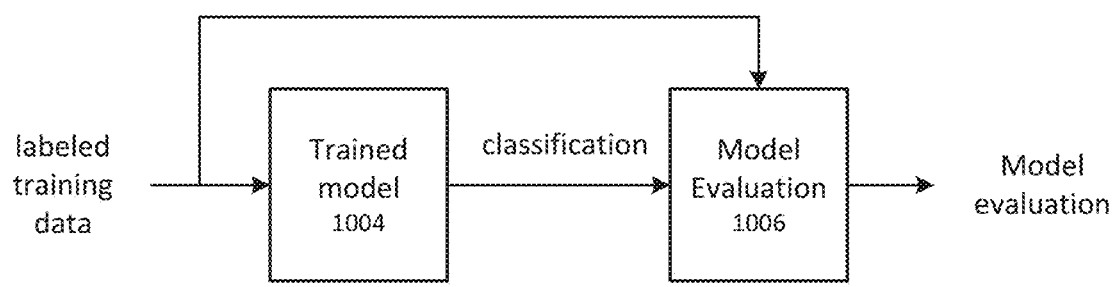
FIG. 10B illustrates a process of validating a machine learning classification technique according to some embodiments.

Referring to FIG. 9, to train a machine learning classification technique, a large number of centroids 908 are randomly generated within a pentagon 900 having vertices at the 40% concentration limits of the five radial axes shown in FIG. 1. Each of the randomly generated centroids is then classified using the composite fault region map shown in FIG. 6 to generate a training label associated with the centroid. The selected machine learning classification technique may then be trained using the labeled training data. Training of a machine learning classification technique is illustrated in FIGS. 10A and 10B. Referring to FIG. 10A, a subset of the labeled training data is provided to a supervised learning classification training system 1002 that generates trained classification model parameters based on the labeled training data. Training of a classification technique using supervised learning is well known in the art, and involves an iterative process in which samples are provided to a model, which generates a classification for the sample. The classification generated by the sample is compared to the label of the sample, and if the classification generated by the model is incorrect, the model parameters are adjusted to reduce the error. The adjustment of model parameters typically involves adjusting one or more model weights to minimize an error function, such as a mean square error (MSE) or other metric.

In this case, the labeled training data comprises a plurality of (x,y) coordinates associated with centroids, and the labels comprise the known classifications associated with the centroids.

This process is repeated for a large number of labeled training data samples until the error rate of classification by the model is within an acceptable range.

Figure 11:
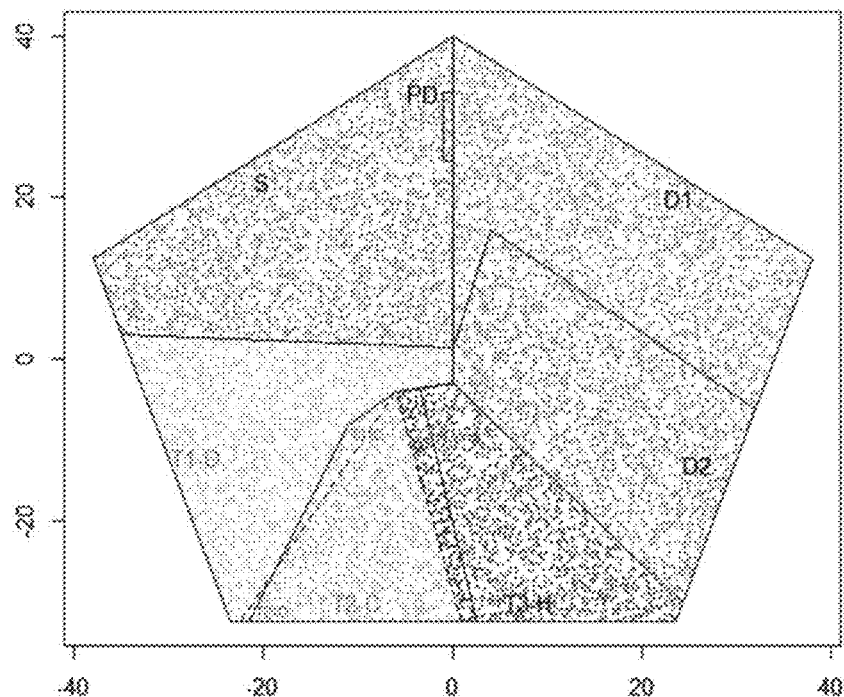
FIG. 11 illustrates the results of classification of centroids using a trained machine learning classification technique according to some embodiments.

The model parameters output by the supervised learning classification training system are used to implement a trained classification model. Referring to FIG. 10B, a trained classification model 1004 may be tested by supplying additional labeled training data to the trained classification model 1004, which generates classifications of the input data. The classifications generated by the trained classification model 1004 are provided to a model evaluation system 1006 along with the labels of the labeled training data, which are the known classifications of the centroids. The model evaluation system 1006 compares the classifications output by the trained classification model 1004 with the labels and determines an accuracy of the model based on the comparison. FIG. 11 illustrates an example of classification by a trained classification model that shows high agreement with the fault region definitions in the composite fault region map. In the example shown in FIG. 11, a random forest classification model was trained using 124,890 randomly generated centroids that were labeled using the composite fault region map. The trained model was validated using a dataset of 13,872 randomly selected points of the randomly generated centroids. The trained model exhibited an overall accuracy of 99.65%.

Figure 12A:
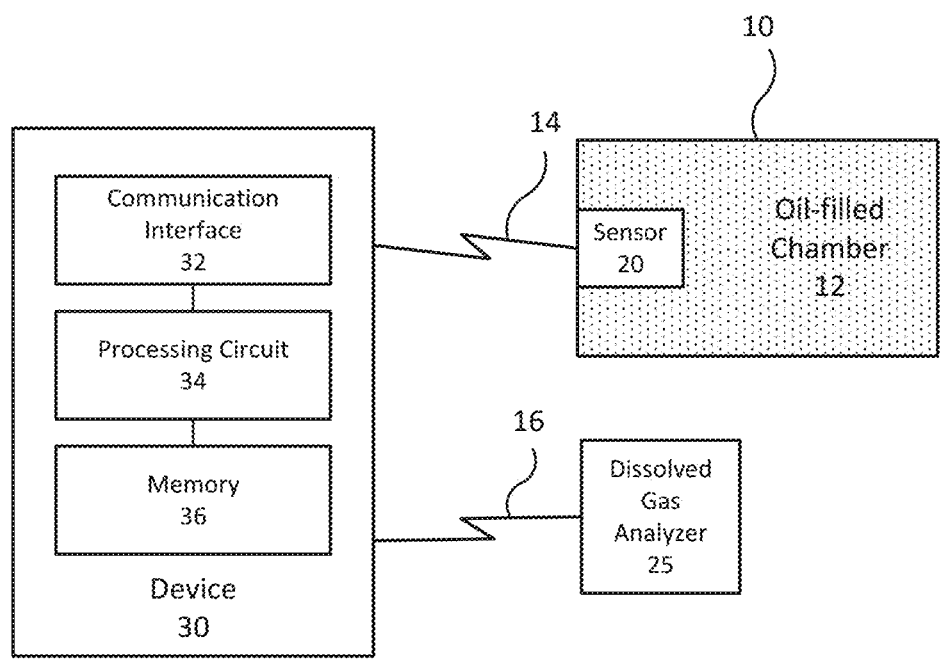
FIG. 12A is a block diagram illustrating a system for performing dissolved gas analysis according to some embodiments.

FIG. 12A is a block diagram of a system including a device 30 for performing fault analysis based on dissolved gas levels and a transformer 10 that contains an oil filled chamber 12. Various embodiments provide a device 30 that includes a processor circuit 34 a communication interface 32 coupled to the processor circuit, and a memory 36 coupled to the processor circuit 34. The memory 36 includes machine-readable computer program instructions that, when executed by the processor circuit, cause the processor circuit to perform some of the operations depicted described herein.

As shown, the device 30 includes a communication interface 32 (also referred to as a network interface) configured to provide communications with other devices, e.g., with a sensor 20 in the transformer 10 via a wired or wireless communication link 14. The device 30 may in some cases communicate with a dissolved gas analyzer (DGA) 25 via a wired or wireless communication link 16 to obtain levels of dissolved gases within the transformer 10. The DGA 25 may analyze samples of oil from the transformer 10 and determine levels of dissolved gases within the transformer 10. The DGA 25 may provide information regarding the dissolved gas levels to the device 30.

The device 30 also includes a processor circuit 34 (also referred to as a processor) and a memory circuit 36 (also referred to as memory) coupled to the processor circuit 34. According to other embodiments, processor circuit 34 may be defined to include memory so that a separate memory circuit is not required.

As discussed herein, operations of the device 30 may be performed by processing circuit 34 and/or communication interface 32. For example, the processing circuit 34 may control the communication interface 32 to transmit communications through the communication interface 32 to one or more other devices and/or to receive communications through network interface from one or more other devices. Moreover, modules may be stored in memory 36, and these modules may provide instructions so that when instructions of a module are executed by processing circuit 34, processing circuit 34 performs respective operations (e.g., operations discussed herein with respect to example embodiments).

The transformer 10, which may for example be a high voltage transformer, includes an oil-filled chamber 12. A sensor 20 is provided within or adjacent the oil-filled chamber 12. The sensor measures concentrations of one or more dissolved gases, such as Hz, $C_2H_2$, $C_2H_4$, $CH_4$, and $C_2H_6$, and transmits the measurements via a communication channel 14 to the device 30. The communication links 14, 16 may include a wired or wireless channel, and in some embodiments may include a wireless local area network (WLAN) or cellular communication network, such as a 4G or 5G communication network.

The device 30 may receive on-line or off-line measurements of dissolved gas levels from transformers 10 and process the measurements to identify fault conditions in the transformers 10. Although depicted as a standalone device, the device 30 may be implemented in a server, in a server cluster and/or a cloud-based remote server system that provides asset monitoring. Dissolved gas data may be obtained by the device 30 from one transformer and/or from multiple transformers. In particular, it may be desirable to receive training data from multiple transformers.

A device 30 as described herein may be implemented in many different ways. For example, a device 30 according to some embodiments may receive online/offline data, and the received data used by a machine learning technique configured in the device for learning and classification. The device may be connectable to one transformer 10 or to a DGA 25 to receive data regarding dissolved gas levels.

In some embodiments, the device 30 may be connectable to receive data relating to several transformers 10.

In some embodiments, a device 10 may be configured as a software module in a remote server (or cloud server), where the server is receiving online/offline data and the server having machine learning modules for learning and classification, wherein the device 10 in the server is connectable to receive data relating to several transformers.

Figure 12B:
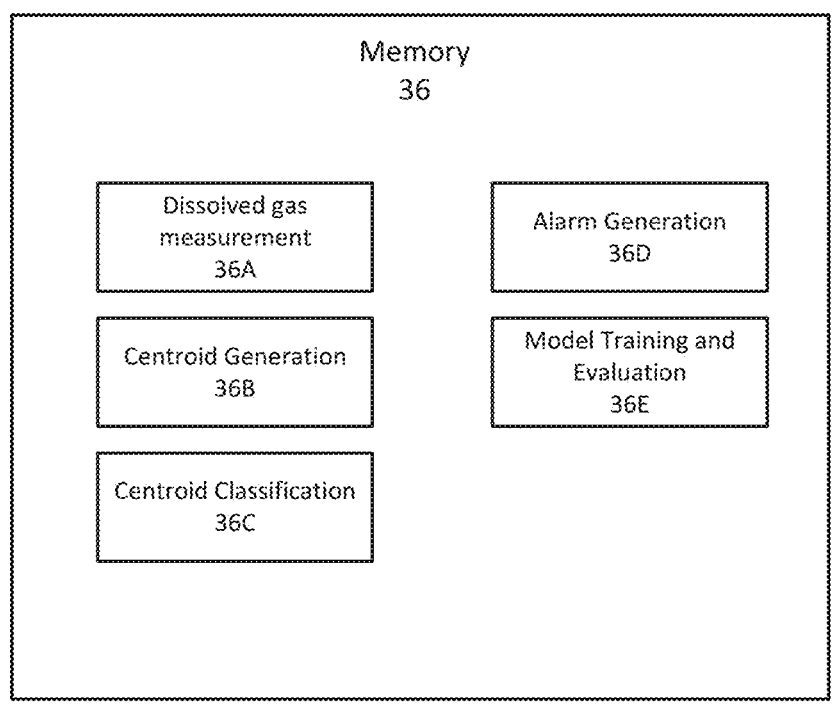
FIG. 12B is a block diagram illustrating functional modules of a system for performing dissolved gas analysis according to some embodiments.

FIG. 12B illustrates various functional modules that may be store in the memory 36 of the device 30. The modules may include a dissolved gas measurement module 36A for obtaining dissolved gas measurements from a sensor 20 in the transformer 10 and/or from the DGA 25 via the communication interface 32, a centroid generation module 36B that generates centroids based on the dissolved gas measurements, and a centroid classification module 36C that classifies faults based on the centroids generated by the centroid generation module 36B.

Some embodiments may further include an alarm generation module 36D that generates an alarm in response to the classification of a centroid. For example, the classification of a centroid may indicate that a critical fault has occurred in the transformer 10. An alarm may be generated to notify personnel of the fault so that the fault can be addressed. Some embodiments may further deactivate or disable the transformer 10 in response to the classification by sending a control signal to the transformer 10 via the communication channel 14.

Some embodiments may further include a model training and evaluation module 36E that trains a machine learning model to perform the classification of centroids and/or of dissolved gas measurements. It will be appreciated that the functionality defined by the modules 36A to 36E may be performed in one or multiple devices and/or in cloud-based or virtual environments.

Figure 13:
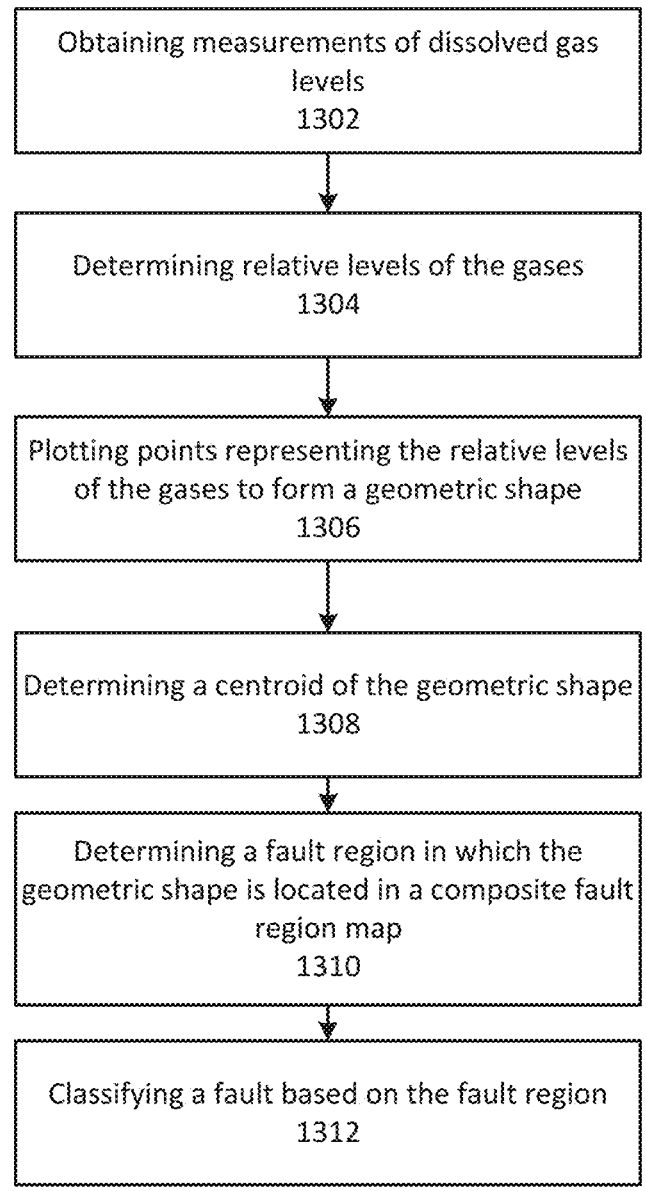
FIG. 13 illustrates operations of systems/methods according to some embodiments.

FIG. 13 illustrates operations of systems/methods according to some embodiments. In particular, the operations illustrated in FIG. 13 may be performed by a device 30 as illustrated in FIG. 12A.

Referring to FIG. 13, a method of analyzing dissolved gas in an oil-filled transformer includes obtaining measurements of dissolved gas levels of a first number of gases in the oil-filled device (block 1302), determining relative levels of the first number of gases (block 1304), and plotting a first number of points representing each of the relative levels of the first number of gases on a respective one of a first number of radial axes, each of the first number of radial axes being equally angularly spaced around an origin in a two dimensional coordinate system, each of the first number of radial axes representing a relative level of one of the first number of gases, the first number of points forming a polygon within the two dimensional coordinate system (block 1306).

The method further includes determining a centroid of the polygon (block 1308). A fault region in which the centroid of the polygon is located is determined out of a plurality of fault regions defined in the two dimensional coordinate system (block 1310). The plurality of fault regions are defined in a composite fault region map that is a composite of a first fault region map that defines regions that classify basic electrical faults within the oil-filled transformer that do not involve carbonization of cellulose within the oil-filled transformer and a second fault region map that defines regions that classify faults at least partially based on carbonization of cellulose within the oil-filled transformer. The method further includes classifying a fault experienced by the oil-filled transformer based on the determined fault region within the composite fault region map (block 1312).

In some embodiments, the first number is five, the polygon includes a pentagonal shape, the first fault region map includes a first Duval pentagon, and the second fault region map includes a second Duval pentagon.

In some embodiments, the composite fault region map includes regions that classify thermal faults based on both thermal properties and carbonization of cellulose within the oil-filled transformer.

In some embodiments, the first number of gases includes at least $CH_4$ and $C_2H_4$, the first Duval pentagon defines fault regions associated at least in part with the presence of $CH_4$ and $C_2H_4$ based on temperature, the second Duval pentagon defines fault regions associated at least in part with the presence of $CH_4$ and $C_2H_4$ based on carbonization, and the composite fault region map defines fault regions associated at least in part with the presence of $CH_4$ and $C_2H_4$ based on a combination of temperature and carbonization.

In some embodiments, the first number of gases includes at least $CH_4$ and $C_2H_4$, the first Duval pentagon defines fault regions associated at least in part with the presence of $CH_4$ and $C_2H_4$ of T1, T2, and T3, the second Duval pentagon defines fault regions associated at least in part with the presence of $CH_4$ and $C_2H_4$ of O, C, and T3-H, and the composite fault region map defines fault regions associated at least in part with the presence of $CH_4$ and $C_2H_4$ that are coterminous within the fault regions of T1, T2 and T3 in the first Duval pentagon and the fault regions of O, C, and T3-H in the second Duval pentagon.

In some embodiments, the fault regions within the composite fault region map include T1-O, T2-O, T1-C, T2-C, T3-C and T3-H.

In some embodiments, the first number of gases include $C_2H_2$ plotted on a first axis that extends at an angle of 18 degrees relative to an x-axis of the two dimensional coordinate system, $H_2$ plotted on a second axis that extends at an angle of 90 degrees relative to the x-axis of the two dimensional coordinate system, $C_2H_6$ plotted on a third axis that extends at an angle of 162 degrees relative to the x-axis of the two dimensional coordinate system, $CH_4$ plotted on a fourth axis that extends at an angle of 234 degrees relative to the x-axis of the two dimensional coordinate system, and $C_2H_4$ plotted on a fifth axis that extends at an angle of 306 degrees relative to the x-axis of the two dimensional coordinate system.

In some embodiments, the fault regions within the composite fault region map have the following coordinates in the two-dimensional coordinate system wherein the relative levels of the first number of gases are plotted as relative percentages of the first number of gases:

T1-O: [(−35, 3.1), (0, 1.5), (0, −3), (−3.5, −3.5), (−6, −4), (−11, −8), (−18.8, −26), (−22.5, −32.4), (−23.5, −32.4)]
T2-O: [(−21.5, −32.4), (−18.8, −26), (−22.5, −32.4)]
T1-C: [(−6, −4), (−11, −8), (−18.8, −26)]
T2-C: [(−6, −4), (−18.8, −26), (−21.5, −32.4), (1, −32.4)]
T3-C: [(−3.5, −3.5), (−6, −4), (1, −32.4), (2.5, −32.4)]
T3-H: [(−3.5, −3.5), (2.5, −32.4), (23.5, −32.4), (24.3, −30), (0, −3)].

In some embodiments, determining the fault region in which the centroid of the polygon is located includes inputting the centroid of the polygon into a machine learning classification technique that generates, as an output, a classification of the fault region associated with the centroid.

In some embodiments, the machine learning classification technique was trained via supervised learning using an input data set including a plurality of centroids and associated fault regions.

In some embodiments, the machine learning classification technique includes a random forest technique. In some embodiments, the machine learning classification technique includes a gradient boosting machine technique.

In some embodiments, the method includes activating an alarm in response to classifying the fault. For example, the classification of a centroid may indicate that a critical fault has occurred in the transformer 10, such as a fault involving carbonization of paper that could lead to a fire hazard. An alarm may be generated to notify personnel of the fault so that the fault can be addressed and remediated. For example, an alert may indicate that a serious issue has been identified from DGA results that indicates an electrical fault of high intensity (e.g., temperature>500 C). The alert may provide a recommended action, such as removing the transformer 10 from operation and performing a thorough internal inspection.

Some embodiments may automatically deactivate or disable the transformer 10 in response to the classification by sending a control signal to the transformer 10 via the communication channel 14.

In some embodiments, a machine learning classification technique may be trained to classify faults based on detected concentrations of one or more diagnostic gases without using a graphical approach such as a fault region map. A graphical approach as described above reduces dimensionality of the input data from five (e.g., the concentrations of the five diagnostic gases) to two (the coordinates of the centroid of a polygon formed by the concentrations of the five diagnostic gases). This reduction in dimensionality may cause the classification system to lose accuracy, at least in part because, as noted above, a centroid is not necessarily unique, since different polygons could have the same centroid. Accordingly, some embodiments provide a training data set that includes the concentrations of the diagnostic gases along with a classification of a fault associated with the combination of concentrations of the diagnostic gases as the label.

Referring again to FIG. 10A, in some embodiments, a machine learning classification model is trained via supervised learning using the training data set to generated model parameters for the classification model. The classification model may be a random forest model or other suitable classification model.

Figure 14:
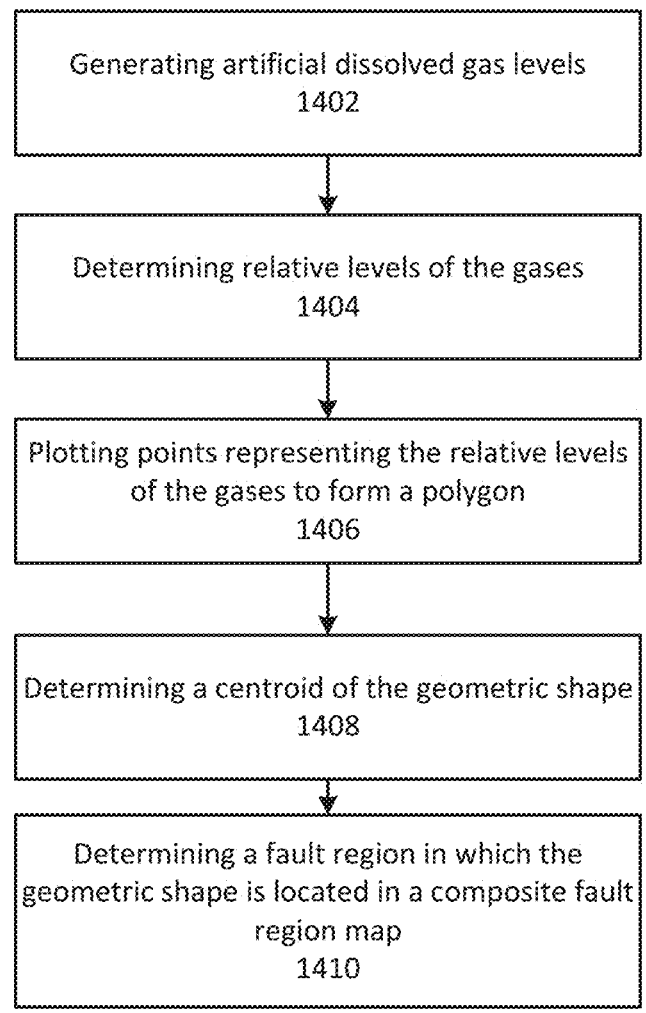
FIG. 14 illustrates operations of systems/methods according to further embodiments.

It will be appreciated that to accurately train a machine learning classification model, it is desirable to use many thousands of training data points. For problems such as classifying faults based on dissolved gases in transformers, it may be impractical to obtain enough data points to accurately train the technique. Accordingly, some training data points may be generated using a fault region map, such as the composite fault region map shown in FIG. 6. That is, referring to FIG. 14, training data may be generated by generating artificial dissolved gas concentrations of a plurality of diagnostic gases (block 1402) and determining relative levels of the dissolved gases (block 1404). The artificial dissolved gas concentrations may be generated randomly, pseudo-randomly, by a determinative technique, and/or by a combination of random, pseudo-random and/or determinative means.

The relative levels of the dissolved gas concentrations are plotted to form polygons (block 1406), determining centroids of the polygons (block 1408), and determining a fault region in which the centroid lies based on a fault region map such as the composite fault region map described above (block 1410). The resulting data may then be used as training data for training a machine learning classification system.

Figure 15:
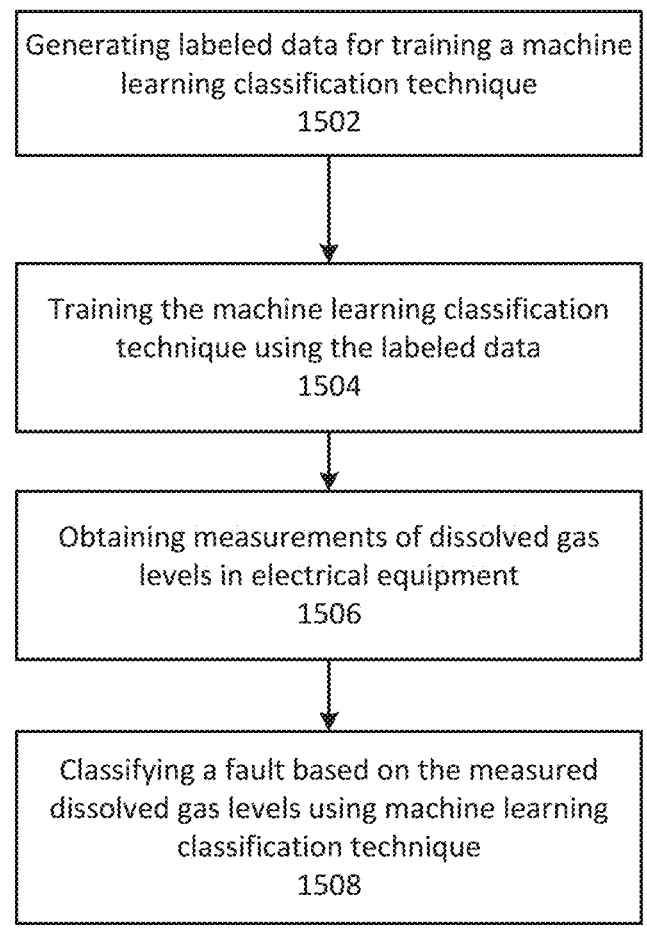
FIG. 15 illustrates operations of systems/methods according to further embodiments.

Operations of such a machine learning classification system are illustrated in FIG. 15. As shown therein, a method of performing dissolve gas analysis includes generating or obtaining labeled training data for the machine learning classification technique (block 1502). The training data may be obtained from on-line or off-line analysis of actual fault events, from classification of randomly generated gas levels as described above, and/or a combination of real and randomly generated data points. The method then trains a machine learning classification technique, such as a random forest classification technique, using the labeled training data (block 1504).

Once the machine learning classification technique has been trained, the method includes obtaining measurements of dissolved gas concentrations in a transformer 10. The measurements may be obtained, for example via a sensor 20 as shown in FIG. 12A or through other means, such as off-line data collection. The method then classifies a fault associated with the dissolved gas measurements using the machine learning classification technique that takes as inputs the dissolved gas concentrations and generates a classification of a fault associated with the dissolved gas concentrations. The classification may, for example, correspond to one of the regions in the composite fault region map shown in FIG. 6.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components, or functions but does not preclude the presence or addition of one or more other features, integers, elements, steps, components, functions, or groups thereof.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the examples of embodiments and their equivalents, and shall not be restricted or limited by the foregoing detailed description.

What is claimed is:

1. A method of analyzing dissolved gas in an oil-filled transformer, comprising:
    obtaining measurements of dissolved gas levels of a first number of gases in the oil-filled transformer;
    determining relative levels of the first number of gases;
    plotting a first number of points representing each of the relative levels of the first number of gases on a respective one of a first number of radial axes, each of the first number of radial axes being equally angularly spaced around an origin in a two dimensional coordinate system, each of the first number of radial axes representing a relative level of one of the first number of gases, the first number of points forming a polygon within the two dimensional coordinate system;
    determining a centroid of the polygon;
    determining a fault region in which the centroid of the polygon is located, out of a plurality of fault regions defined in the two dimensional coordinate system, wherein the plurality of fault regions are defined in a composite fault region map that is a composite of a first fault region map that defines regions that classify basic electrical faults within the oil-filled transformer, wherein the definition of regions in the first fault region map is not based on carbonization of cellulose within the oil-filled transformer, and a second fault region map that defines regions that classify faults at least partially based on carbonization of cellulose within the oil-filled transformer, wherein determining the fault region in which the centroid of the polygon is located comprises inputting the centroid of the polygon into a machine learning classification technique that generates, as an output, a classification of the fault region associated with the centroid, wherein the machine learning classification technique comprises a gradient boosting machine technique; and
    classifying a fault experienced by the oil-filled transformer based on the determined fault region within the composite fault region map;
    wherein the first Duval pentagon defines fault regions of T1, T2, and T3, the second Duval pentagon defines fault regions of O, C, and T3-H, and the composite fault region map defines fault regions that are coterminous within the fault regions of T1, T2 and T3 in the first Duval pentagon and the fault regions of O, C, and T3-H in the second Duval pentagon.

2. The method of claim 1, wherein the first number is five, the polygon comprises a pentagonal shape, the first fault region map comprises a first Duval pentagon, and the second fault region map comprises a second Duval pentagon.

3. The method of claim 2, wherein the composite fault region map comprises regions that classify thermal faults based on both thermal properties and carbonization of cellulose within the oil-filled transformer.

4. The method of claim 3, wherein the first Duval pentagon defines fault regions based on temperature, the second Duval pentagon defines fault regions at least in part based on carbonization, and the composite fault region map defines fault regions based on a combination of temperature and carbonization.

5. The method of claim 1, wherein the fault regions within the composite fault region map comprise T1-O, T2-O, T1-C, T2-C, T3-C and T3-H.

6. The method of claim 1, wherein the first number of gases comprise:
    $C_2H_2$ plotted on a first axis that extends at an angle of 18 degrees relative to an x-axis of the two dimensional coordinate system;
    $H_2$ plotted on a second axis that extends at an angle of 90 degrees relative to the x-axis of the two dimensional coordinate system;
    $C_2H_6$ plotted on a third axis that extends at an angle of 162 degrees relative to the x-axis of the two dimensional coordinate system;
    $CH_4$ plotted on a fourth axis that extends at an angle of 234 degrees relative to the x-axis of the two dimensional coordinate system; and
    $C_2H_4$ plotted on a fifth axis that extends at an angle of 306 degrees relative to the x-axis of the two dimensional coordinate system.

7. The method of claim 6, wherein the fault regions within the composite fault region map have the following coordinates in the two-dimensional coordinate system when the relative levels of the first number of gases are plotted as relative percentages of the first number of gases:
    T1-O: [(−35, 3.1), (0, 1.5), (0, −3), (−3.5, −3.5), (−6, −4), (−11, −8), (−18.8, −26), (−22.5, −32.4), (−23.5, −32.4)]
    T2-O: [(−21.5, −32.4), (−18.8, −26), (−22.5, −32.4)]
    T1-C: [(−6, −4), (−11, −8), (−18.8, −26)]
    T2-C: [(−6, −4), (−18.8, −26), (−21.5, −32.4), (1, −32.4)]
    T3-C: [(−3.5, −3.5), (−6, −4), (1, −32.4), (2.5, −32.4)]
    T3-H: [(−3.5, −3.5), (2.5, −32.4), (23.5, −32.4), (24.3, −30), (0, −3)].

8. The method of claim 1, wherein the machine learning classification technique was trained via supervised learning using an input data set comprising a plurality of artificially generated centroids and associated fault regions.

9. The method of claim 1, further comprising:
    deactivating the oil-filled transformer in response to classifying the fault.

10. The method of claim 1, wherein obtaining measurements of dissolved gas levels of the first number of gases in the oil-filled transformer comprises receiving sensor measurements from a sensor in the oil-filled transformer.

11. A method of training a machine classification learning technique, comprising:
    generating a plurality of sets of artificial dissolved gas concentrations of a first number of diagnostic gases;
    determining relative levels of the artificial dissolved gas concentrations;
    plotting a first number of points representing each of the relative levels of the artificial dissolved gas concentrations on a respective one of a first number of radial axes, each of the first number of radial axes being equally angularly spaced around an origin in a two dimensional coordinate system, each of the first number of radial axes representing a relative level of one of the first number of diagnostic gases, the first number of points forming a polygon within the two dimensional coordinate system;
    determining a centroid of the polygon;

determining a fault region in which the centroid of the polygon is located, out of a plurality of fault regions defined in the two dimensional coordinate system;

classifying a fault experienced by an oil-filled transformer based on the determined fault region within the composite fault region map; and training a machine learning classification technique using the plurality of sets of artificial dissolved gas concentrations of a first number of diagnostic gases and associated faults as labeled training data, wherein the machine learning classification technique comprises a gradient boosting machine technique;

wherein the plurality of fault regions are defined in a composite fault region map that is a composite of a first fault region map that defines regions that classify basic electrical faults within the oil-filled transformer, wherein the definition of regions in the first fault region map is not based on carbonization of cellulose within the oil-filled transformer, and a second fault region map that defines regions that classify faults at least partially based on carbonization of cellulose within the oil-filled transformer;

wherein the first fault region map defines fault regions of T1, T2, and T3, the second fault region map defines fault regions of O, C, and T3-H, and the composite fault region map defines fault regions that are coterminous within the fault regions of T1, T2 and T3 in the first fault region map and the fault regions of O, C, and T3-H in the second fault region map.

12. The method of claim 11, further comprising:
obtaining measurements of dissolved gas levels of the diagnostic gases in the oil-filled transformer; and
classifying the fault of the oil-filled transformer using the machine learning classification technique.

13. The method of claim 12, wherein obtaining measurements of dissolved gas levels of the first number of diagnostic gases in the oil-filled transformer comprises receiving sensor measurements from a sensor in the oil-filled transformer.

14. The method of claim 11, further comprising:
deactivating the oil-filled transformer in response to classifying the fault.

15. A device for performing dissolved gas analysis, comprising:
a processing circuit; and
a memory coupled to the processing circuit, wherein the memory comprises computer readable program instructions that, when executed by the processing circuit, cause the device to perform operations comprising:
obtaining measurements of dissolved gas levels of a first number of gases in an oil-filled transformer;
determining relative levels of the first number of gases;
plotting a first number of points representing each of the relative levels of the first number of gases on a respective one of a first number of radial axes, each of the first number of radial axes being equally angularly spaced around an origin in a two dimensional coordinate system, each of the first number of radial axes representing a relative level of one of the first number of gases, the first number of points forming a polygon within the two dimensional coordinate system;
determining a centroid of the polygon;
determining a fault region in which the centroid of the polygon is located, out of a plurality of fault regions defined in the two dimensional coordinate system, wherein the plurality of fault regions are defined in a composite fault region map that is a composite of a first fault region map that defines regions that classify basic electrical faults within the oil-filled transformer that do not involve carbonization of cellulose within the oil-filled transformer and a second fault region map that defines regions that classify faults at least partially based on carbonization of cellulose within the oil-filled transformer, wherein determining the fault region in which the centroid of the polygon is located comprises inputting the centroid of the polygon into a machine learning classification technique that generates, as an output, a classification of the fault region associated with the centroid, wherein the machine learning classification technique comprises a gradient boosting machine technique; and
classifying a fault experienced by the oil-filled transformer based on the determined fault region within the composite fault region map;
wherein the first fault region map defines fault regions of T1, T2, and T3, the second fault region map defines fault regions of O, C, and T3-H, and the composite fault region map defines fault regions that are coterminous within the fault regions of T1, T2 and T3 in the first fault region map and the fault regions of O, C, and T3-H in the second fault region map.

16. The device of claim 15, wherein the device is provided in a cloud-based service infrastructure, a standalone server or a server cluster.

17. The device of claim 15, wherein the device is connectable to a sensor or a dissolved gas analyzer for obtaining the measurements of dissolved gas levels of the first number of gases in the oil-filled transformer.

* * * * *